US009659679B2

(12) United States Patent
McIntyre et al.

(10) Patent No.: US 9,659,679 B2
(45) Date of Patent: May 23, 2017

(54) COMPOSITE FILAR FOR IMPLANTABLE MEDICAL DEVICE

(71) Applicant: Medtronic, Inc., Minneapolis, MN (US)

(72) Inventors: Peter B. McIntyre, Mounds View, MN (US); Jacob L. Popp, Maplewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/695,724

(22) Filed: Apr. 24, 2015

(65) Prior Publication Data

US 2016/0111178 A1    Apr. 21, 2016

Related U.S. Application Data

(60) Provisional application No. 62/066,458, filed on Oct. 21, 2014.

(51) Int. Cl.

| | |
|---|---|
| *A61N 1/00* | (2006.01) |
| *H01B 1/02* | (2006.01) |
| *H01B 5/08* | (2006.01) |
| *A61N 1/05* | (2006.01) |
| *A61L 31/02* | (2006.01) |
| *A61L 31/08* | (2006.01) |

(52) U.S. Cl.
CPC .............. *H01B 1/02* (2013.01); *A61L 31/022* (2013.01); *A61L 31/088* (2013.01); *A61N 1/05* (2013.01); *A61N 1/056* (2013.01); *A61N 1/0509* (2013.01); *A61N 1/0531* (2013.01); *A61N 1/0534* (2013.01); *A61N 1/0551* (2013.01); *H01B 5/08* (2013.01); *A61L 2420/08* (2013.01)

(58) Field of Classification Search
CPC ....... H01B 1/02; A61L 31/022; A61L 31/088; A61N 1/05; A61N 1/0509; A61N 1/0531; A61N 1/056
See application file for complete search history.

(56) References Cited

U.S. PATENT DOCUMENTS

| | | | |
|---|---|---|---|
| 4,938,922 | A | 7/1990 | Mizuhara |
| 5,630,840 | A | 5/1997 | Mayer |
| 7,015,392 | B1 | 3/2006 | Dickenson |
| 7,280,875 | B1 | 10/2007 | Chitre et al. |
| 7,532,939 | B2 | 5/2009 | Sommer et al. |
| 7,601,033 | B2 | 10/2009 | Ries et al. |
| 7,612,291 | B2 | 11/2009 | Chastain et al. |
| 7,654,843 | B2 | 2/2010 | Olson et al. |
| 7,783,365 | B2 | 8/2010 | Ebert et al. |
| 7,860,580 | B2 | 12/2010 | Falk et al. |
| 8,005,549 | B2 | 8/2011 | Boser et al. |

(Continued)

OTHER PUBLICATIONS (PCT/US2015/056324) PCT Notification of Transmittal of the International Search Report and the Written Opinion of the International Searching Authority, mailed Mar. 23, 2016, 25 pages.

(Continued)

*Primary Examiner* — Scott Getzow
(74) *Attorney, Agent, or Firm* — Carol F. Barry

(57) ABSTRACT

A composite filar has a conductive core, an outer fatigue-resistant metallic layer and a diffusion barrier between the core and the fatigue-resistant layer to prevent intermetallic diffusion between the core and the fatigue-resistant layer.

18 Claims, 8 Drawing Sheets

(56) References Cited

U.S. PATENT DOCUMENTS

| | | |
|---|---|---|
| 8,337,750 B2 | 12/2012 | Jablokov et al. |
| 8,340,759 B2 | 12/2012 | McIntyre et al. |
| 8,639,352 B2 | 1/2014 | Wang et al. |
| 8,660,662 B2 | 2/2014 | Li et al. |
| 8,755,909 B2 | 6/2014 | Sommer et al. |
| 8,825,180 B2 | 9/2014 | Bauer et al. |
| 2012/0271386 A1 | 10/2012 | Li et al. |
| 2014/0142672 A1 | 5/2014 | Wang et al. |

OTHER PUBLICATIONS (PCT/US2015/056324) Invitation to Pay Additional Fees and, Where Applicable, Protest Fees, Dec. 17, 2015, 10 pages.

Gold, Wikipedia, Dec. 6, 2015, printed Aug. 12, 2015, 29 pages, https://en/wikipedia.org.wiki/gold.

Palladium, Dec. 4, 2015, printed Aug. 12, 2015, 12 pages, https://en/wikipedia.org.wiki/palladium.

"Fatigue Performance and Microstructure of Pt-20Ir Wire and Is Coil for Medical Device Application", by Bernard Li et al., ASME 2012 International Mechanical Engineering Congress and Exposition, Jan. 1, 2013, 9 pages.

ASTM International, "Standard Specification for Wrought Titanium-15 Molybdenum Alloy for Surgical Implant Applications (UNS R58150)," Standard Designation: F 2066-08; Copyright 2008 ASTM International: West Conshohocken, PA, United States. 5 pages.

COMPOSITE FILAR FOR IMPLANTABLE MEDICAL DEVICE

RELATED APPLICATION

This application claims the benefit of U.S. Provisional Patent Application No. 62/066,458 filed on Oct. 21, 2014, which application is hereby incorporated herein by reference to the extent that it does not conflict with the present disclosure.

FIELD

This disclosure generally relates to, among other things, conductive filars for use in implantable medical devices, particularly for use in implantable medical leads.

BACKGROUND

Implantable medical leads employ conductive filars to transmit electrical signals along the length of the lead. Good conductance and fatigue performance of the filars can be important for the performance and longevity of the lead.

Certain metallic materials exhibit good fatigue performance, but may not be sufficiently conductive for use as the sole material in a filar. Other materials may be sufficiently conductive, but may not exhibit suitable fatigue performance for use as the sole material in a filar.

SUMMARY

This disclosure describes, among other things, composite filars for use in implantable medical devices, such as implantable medical leads, that exhibit good conductance and fatigue performance. The filars include a conductive core and a fatigue-resistant metallic material disposed around the core. However, in some cases the core material and the fatigue-resistant metallic material can become embrittled when in contact during a process of drawing the composite filar. Accordingly, the composite filars described herein include a metallic diffusion barrier layer between the core and the fatigue-resistant metallic layer to prevent intermetallic diffusion between the core and the fatigue-resistant layer. In some embodiments, the diffusion barrier layer comprises radiopaque material, which provides not only good conductivity and fatigue resistance but also visibility via, e.g., fluoroscopy.

In some embodiments, a composite filar for using in an implantable medical device includes a metallic core having a resistivity of less than 25 micro-ohm-cm, a metallic diffusion barrier disposed about and in contact with the core, and a fatigue-resistant metallic layer disposed about and in contact with the metallic diffusion barrier. The materials of the core and the fatigue-resistant metallic layer, if in contact during a drawing process, would undergo intermetallic diffusion to create a more brittle alloy/intermetallic layer. The diffusion barrier prevents intermetallic diffusion between the core and the fatigue-resistant layer. In various embodiments, the fatigue performance of the filar is at least three times greater than a similar filar that does not include the fatigue-resistant metallic layer disposed about the core.

For purposes of the present disclosure, a "similar filar that does not include the fatigue-resistant metallic layer disposed about the diffusion barrier" is a filar that is formed of the same components, except for the fatigue-resistant metallic layer, and in the same manner as the filar having the fatigue-resistant metallic layer, except for manufacturing processes associated with incorporating the fatigue-resistant metallic layer.

In some embodiments, a composite filar for use in an implantable medical device includes a core comprising silver, a diffusion barrier disposed about and in contact with the core, and a metallic layer comprising a titanium-molybdenum alloy disposed about and in contact with the diffusion barrier. By way of example, the titanium-molybdenum alloy may be a titanium-15 molybdenum alloy according to ASTM International standard, F 2066-08, Standard Specification for Wrought Titanium-15 Molybdenum Alloy for Surgical Implant Applications (UNS R58150), Oct. 1, 2008. The diffusion barrier comprises an alloy comprising 33% to 37% by weight nickel, 31.5% to 39% by weight cobalt, 9% to 10.5% by weight molybdenum, and 19% to 21% by weight chromium. For example, the diffusion barrier can comprise of ASTM F562 MP35N alloy.

Two or more of the composite filars described herein can be used to form a cable or coil. The composite filars, cables or coils comprising composite filars described herein can be incorporated into implantable medical leads.

One or more embodiments of the systems, leads, cables, filars or methods described herein may provide one or more advantages over prior systems, leads, cables, filars or methods. Such advantages will be readily understood from the summary above and detailed description that follows.

The schematic drawings in are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

This disclosure describes, among other things, composite filars for use in implantable medical devices, such as implantable medical leads, that exhibit good conductance and fatigue performance. The filars include a conductive core, a metallic diffusion barrier layer disposed around the core, and a fatigue-resistant metallic material disposed around the diffusion barrier layer.

The diffusion barrier serves to prevent intermetallic diffusion between the fatigue-resistant layer and the core that would otherwise occur if the fatigue-resistant layer and the core were in contact during a drawing process to form the filar. Prevention of such intermetallic diffusion can be important in improving fatigue performance of the filar, particularly where the intermetallic diffusion would result in a brittle intermetallic layer. Examples of a conductive core material and a fatigue-resistant metallic material that can form a brittle intermetallic layer are silver (Ag) and titanium (Ti) alloys, such as Ti-molybdenum (Ti—Mo) alloys. Other examples, such as silver and tantalum or platinum and tantalum, are known to those of skill in the art. It will be understood that the material selected for the diffusion barrier will depend on the materials selected for the core and the fatigue-resistant layers. Nickel-cobalt-chromium-molybdenum (NiCoCrMo) alloys are examples of a material that can form an effective diffusion barrier to prevent intermetallic diffusion between Ag and Ti alloys. Other diffusion barrier materials for preventing diffusion between Ag and Ti alloys or between other conductive core materials and fatigue-resistant metallic materials are known in the art, such as molybdenum or tantalum.

In various embodiments, the filars described herein are cold drawn. During a cold drawn process, the core and any outer layers are drawn through a die and the outer layer is heated or annealed to relieve stress and to prevent the filar from becoming too brittle. If needed or desired, the filar can be subjected to another cold drawing step (draw through die and heat or anneal). Such cold draw processes are susceptible to intermetallic diffusion due, in large part, to the additional energy available for atom movement (e.g., diffusion) during composite heating. In addition, the ambient or low temperature kinetics of the material system could be such that the two materials will diffuse without the application of additional heat (e.g., gold and nickel).

Figure 1:
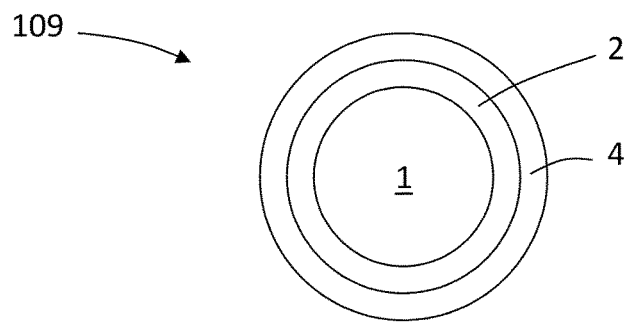
FIG. 1 is a schematic cross-sectional view of an embodiment of a filar.
Figure 2:
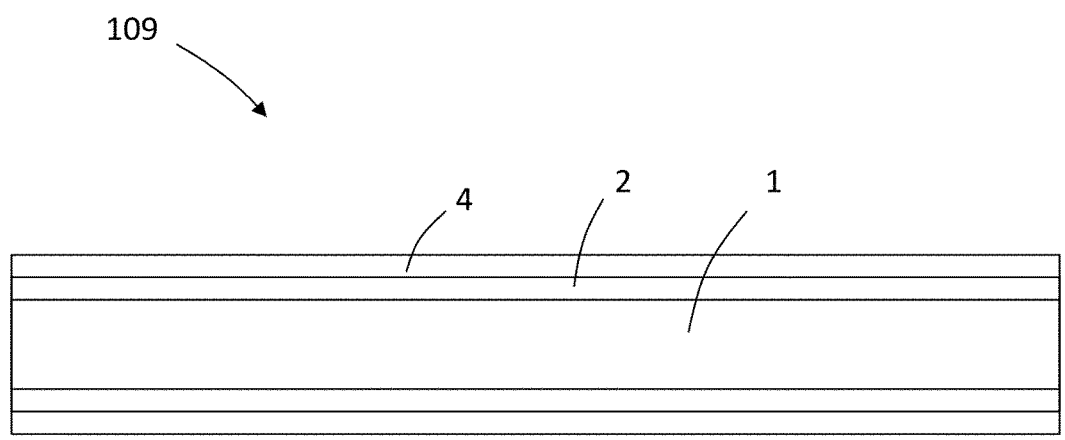
FIG. 2 is a schematic longitudinal sectional view of an embodiment of a filar.

Referring now to FIGS. 1 and 2, cross-sectional (FIG. 1) and longitudinal-sectional (FIG. 2) views of embodiments of filars for use in implantable medical devices are shown. The filars 109 include a metallic conductive core 1, a metallic diffusion barrier 2 disposed about and in contact with the core 1, and a fatigue-resistant metallic layer 4 disposed about and in contact with the diffusion barrier 2. In many embodiments, the metallic conductive core 1, a metallic diffusion barrier 2, and a fatigue-resistant metallic layer 4 are coextensive along the length of the filar 109. In some embodiments, one or more of the diffusion barrier 2 and fatigue-resistant layer 4 are removed along a portion of the length of the filar 109 where electrical contact with, for example, an electrode is made or to form an electrode. In such embodiments, the metallic diffusion barrier 2, and a fatigue-resistant metallic layer 4 are considered coextensive along the length of the filar 109 for purposes of the present disclosure.

In some embodiments, the core 1 is formed of a material having a resistivity of less than 25 micro-ohm-cm ($\mu\Omega$-cm). In some embodiments, the core 1 is formed from material having a resistivity of from about 10 $\mu\Omega$-cm to about 20 $\mu\Omega$-cm. Examples of material having low resistivity that may be included in or form the core include one or more of silver; tantalum, a tantalum alloy comprising one or more of Mo, Nb, Zr, W and Pd; niobium, a niobium alloy comprising one or more of Ta, Mo, Zr, W, Pt, and Pt); platinum; a platinum alloy; palladium; a palladium alloy comprising one or both of Re and Rh; and gold. In some embodiments, the core consists essentially of, or consists of, silver. Silver is a cost effective metallic material that is particularly well suited for cold drawing due to its ductility.

In some embodiments, the fatigue-resistant metallic layer 4 increases the fatigue resistance of the filar three-fold or more relative to a similar filar that does not include the fatigue-resistant metallic layer disposed about the diffusion barrier 2. In some embodiments, the fatigue-resistant metallic layer increases the fatigue resistance of the filar five-fold or more, such as ten-fold or more or 20-fold or more. Fatigue performance of the filar and a similar filar that does not include the fatigue-resistant metallic layer disposed about the diffusion barrier layer 2 can be tested by any suitable method. In some embodiments, fatigue performance is determined by ASTM E2948-14, Standard Test Method for Conducting Rotating Bending Fatigue Tests of Solid Round Fine Wire, ASTM International, West Conshohocken, Pa., 2014.

Examples of materials known to have good fatigue performance include titanium alloys comprising one or more of molybdenum, niobium, tantalum, zirconium, chromium, iron and tin. Ti—Mo alloys, such as titanium-15 molybdenum alloy according to ASTM International standard, F 2066-08, Standard Specification for Wrought Titanium-15 Molybdenum Alloy for Surgical Implant Applications (UNS R58150), Oct. 1, 2008, are well-known biocompatible alloys having good fatigue resistance. In some embodiments, the fatigue-resistant metallic layer has an elastic modulus metallic layer having an elastic modulus of less than 150 Giga-Pascals (GPa), such as ranging from 30 GPa to 90 GPa. A number of titanium alloys, such as those described above, can have such an elastic modulus.

Any suitable material or combination of material can be used as the metallic diffusion barrier 2. As discussed above, the material or materials selected for use in the diffusion barrier 2 are selected based on their ability to prevent intermetallic diffusion between the core 1 and the fatigue-resistant layer 4. One of skill in the art will recognize materials suitable for serving as the barrier layer 2. By way of example, if the core comprises silver (Ag) and the fatigue-resistant metallic layer comprises a Ti-15Mo alloy, such as an alloy according to ASTM F 2066-08, the barrier layer 2 can comprise Mo or a NiCoCrMo alloy. For cold drawing, a NiCoCrMo alloy is preferred because Mo may require heat to be effectively drawn. Examples of suitable NiCoCrMo alloys include alloys comprising 33% to 37% by weight nickel, 31.5% to 39% by weight cobalt, 9% to 10.5% by weight molybdenum, and 19% to 21% by weight chromium. One example of such an alloy is MP35N alloy.

In some embodiments, the diffusion barrier layer includes a radiopaque material. Accordingly, the filar can have suitable conductivity due to the core, suitable fatigue performance due to the fatigue-resistant layer, and be radiopaque due to the barrier layer. Any suitable radiopaque material may be used to form or be included in the diffusion barrier, depending on the materials used for the core and the fatigue-resistant layer. Examples of radiopaque material that may be used in the barrier layer include a NiCoCrMo alloy, such as a MP35N alloy or tantalum (e.g., RO5200).

Other radiopaque materials include metals (e.g., elemental metals or alloys) that include one or more of palladium (Pd), platinum (Pt), gold (Au), silver (Ag), iridium (Ir), nickel (Ni), titanium (Ti), copper (Cu), and zinc (Zn). The use of such radiopaque materials as diffusion barriers will depend on the core material and the fatigue-resistant layer material and the ability of these materials to prevent intermetallic diffusion between the core and the fatigue-resistant layer.

In certain embodiments, the radiopaque material includes metals such as palladium (Pd), platinum (Pt), gold (Au), silver (Ag), or combinations thereof. In certain embodiments, the radiopaque material includes one or more of these metals and optionally one or more of metals such as iridium (Ir), nickel (Ni), titantium (Ti), copper (Cu), zinc (Zn), or combinations thereof.

In certain embodiments, the radiopaque material includes elemental palladium (Pd); elemental platinum (Pt); elemental gold (Au); elemental silver (Ag), and various alloys of one or more of these metals with each other and/or other metals. Examples of alloys include an alloy of platinum (Pt) and iridium (Ir); an alloy of gold (Au), nickel (Ni), and titanium (Ti); an alloy of gold (Au), palladium (Pd), nickel (Ni), and titanium (Ti); an alloy of gold (Au), silver (Ag), copper (Cu), and Zinc (Zn) (e.g., 22 K yellow gold); an alloy of gold (Au) and platinum (Pt) or palladium (Pd) (e.g., 18 K white gold); an alloy of silver (Ag), palladium (Pd), and gold (Au); an alloy of silver (Ag) and platinum (Pt); an alloy of silver (Ag) and gold (Au); an alloy of nickel (Ni) and platinum (Pt).

In the context of alloys, herein, percentages are by mass.

Examples of radiopaque alloys of platinum and iridium include Pt-10Ir alloy (i.e., 90% platinum and 10% iridium) and Pt-20Ir alloy (i.e., 80% platinum and 20% iridium).

Examples of radiopaque alloys of gold (Au), nickel (Ni), and titanium (Ti) include Au—Ni—Ti alloy such as that described in U.S. Pat. No. 4,938,922, which includes the following composition, by weight: 91-99% gold, 0.5-7% nickel; 0.10-2% titanium.

Examples of radiopaque alloys of gold (Au), palladium (Pd), nickel (Ni), and titanium (Ti) include Au—Pd—Ni—Ti alloy such as that described in U.S. Pat. No. 4,938,922, which includes the following composition, by weight: 83-96% gold; 3-10% palladium; 0.5-5% nickel; and 0.10-2% titanium.

Examples of radiopaque alloys of gold (Au), silver (Ag), copper (Cu), and zinc (Zn) include one with the following composition, by weight: 91.67% gold; 5% silver; 2% copper; and 1.33% titanium.

Examples of radiopaque alloys of gold (Au), and platinum (Pt) or palladium (Pd) include those with the following compositions, by weight: 75% gold; and 25% platinum or palladium.

Examples of radiopaque alloys of gold (Au), and platinum (Pt) or palladium (Pd) include one with the following composition, by weight: 75% gold; and 25% platinum or palladium.

Examples of radiopaque alloys of silver (Ag) and gold (Au) include one with the following composition, by weight: 92.5% silver with a touch of gold. This is also called Karat sterling.

Examples of radiopaque alloys of silver (Ag) and platinum (Pt) include one with the following composition, by weight: 93.5% silver; and 6.5% platinum.

Examples of radiopaque alloys of silver (Ag), palladium (Pd), and gold (Au) include one with the following composition, by weight: 95% silver; 1% palladium; and 0.5% gold.

Examples of radiopaque alloys of nickel and platinum include Ni-33Pt alloy, which includes the following composition, by weight: 67% nickel; and 33% platinum.

A filar as described above may have any suitable ratio of cross-sectional area of the core, diffusion barrier and the fatigue-resistant metallic layer to tune the properties of the filar. In some embodiments, the core occupies from about 10% to about 40% of the cross-sectional area of the combined core/diffusion barrier/fatigue-resistant layer, the diffusion barrier occupies from about 10% to about 40% of the cross-sectional area of the combined core/diffusion barrier/fatigue-resistant layer, and the fatigue-resistant layer occupies from about 35% to about 65% of the cross-sectional area of the combined core/diffusion barrier/fatigue-resistant layer. For example, the core can occupy about 25%, the diffusion barrier can occupy about 25% and the fatigue-resistant layer can occupy about 50% of the cross-sectional area of the combined core/diffusion barrier/fatigue-resistant layer.

A filar as described herein may have any suitable outer diameter. In some embodiments, a filar has an outer diameter of about 0.001 inch (0.025 mm) to about 0.01 inch (0.25 mm), such as about 0.002 inch (0.05 mm) to about 0.005 inch (about 0.125 mm) or about 0.003 inch (0.075 mm) to about 0.004 inch (about 0.1 mm). It will be understood that the diameter of the core and thicknesses of the barrier layer and the fatigue-resistant layer may be determined based on the diameter of the filar and the percentage of the cross-sectional area that the core, diffusion barrier and fatigue-resistant layer occupy.

In various embodiments, a filar as described above is cold drawn and the cross-sectional areas of the layers of the filar can be controlled by selecting starting cores and tubes of appropriate cross-sectional area. The filar may be produced in one or more cold drawing steps. In some embodiments, the core is placed within a metallic tube that will form the diffusion barrier. The core and diffusion barrier tube are drawn until a filar of an appropriate diameter is achieved. The resulting filar may then be placed in a metallic tube that will form the fatigue-resistant layer, which assembly can be drawn until a filar having a suitable diameter is achieved. In some embodiments, an MP35N clad silver filar is placed in a Ti-15-Mo metallic tube and drawn. MP35N clad silver filars may be made by any suitable process, such as described in U.S. Pat. No. 7,015,392, or may be purchased from any of a number of suitable vendors including Carpenter Technology Corporation, Wyomissing, Pa., and Fort Wayne Metals, Fort Wayne, Ind.

A wire containing the core and diffusion barrier can be placed in fatigue-resistant metallic tube and drawn through a die structure to result in a wire having a reduced diameter. Thereafter, the wire or filar is annealed by heating. If the fatigue-resistant metallic layer is formed from a Ti alloy, the filar, in various embodiments, is annealed by heating it to at least the beta transit temperature of the selected titanium alloy. At this temperature, the alloy undergoes a phase transformation from the alpha and beta phase to full beta phase. For beta titanium alloys, the beta transit temperature will be in a range of 600° C.-900° C. For instance, in one embodiment, Ti-15Mo has a beta transit temperature of around 730° C. Thus, annealing may occur at from about 730° C. to about 815° C. in one example. This annealing process of using these temperatures to anneal the alloy changes the physical characteristics of titanium alloy tube. That is, it prevents the tube from becoming brittle, and will allow an additional cold-drawing step to be performed without the risk of the tube cracking. Since the annealing temperature of the beta titanium alloy is lower than the melting point of the material used to form the low-resistance core (e.g., silver), the core material will not melt when the wire is annealed.

In some embodiments, the core is placed within a metallic tube that will form the diffusion barrier which is placed within a metallic tube that will form the fatigue-resistant layer. The resulting assembly is drawn in a single drawing process until a filar having a suitable diameter is achieved. Of course, additional drawing steps to achieve a desired diameter may be employed.

One or more of the filars described herein may be included in a strand that can be used to form a cable. The strands or cables may be used to form a conductor for use in an implantable medical device, such as an implantable medical lead.

Figure 3:
FIG. 3 is a schematic perspective view of an embodiment of a parallel strand including at least one filar.

Referring now to FIG. 3, a strand 200 of filars 109 is shown. A strand 200 may include any number of filars 100. In some embodiments (not depicted), a strand 200 consists of one filar 109.

Figure 4:
FIG. 4 is a schematic perspective view of an embodiment of a twisted strand including at least two filars.

As shown in FIG. 4 a strand 200 of two or more filars 109 can be a twisted strand in which the wires are twisted relative to one another. The filars 109 may also be braided to form a braided strand (not shown). A strand can contain any suitable numbers of filars. In some embodiments, a strand includes three, five, seven, or nineteen filars.

Figure 5:
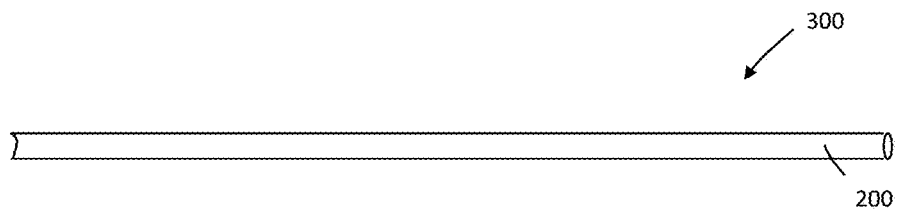
FIG. 5 is a schematic perspective view of an embodiment of a conductor, where the conductor is a strand.
Figure 6:
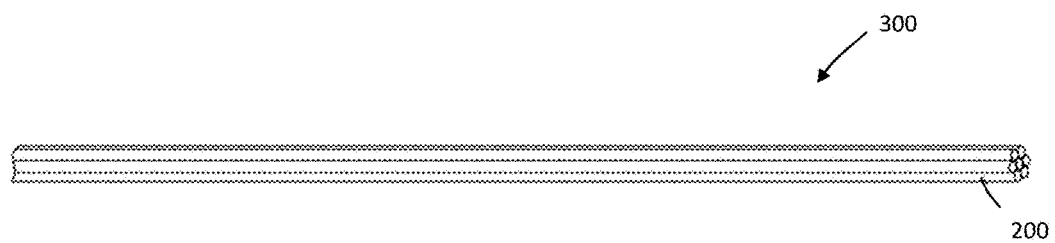
FIG. 6 is a schematic perspective view of an embodiment of a conductor having parallel strands.
Figure 7:
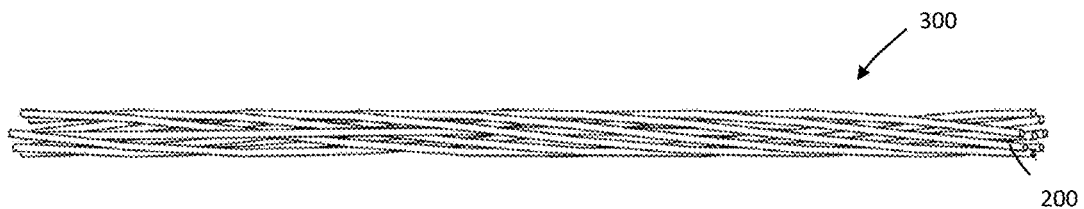
FIG. 7 is a schematic perspective view of an embodiment of a conductor having strands twisted around one another.

Referring now to FIG. 5, a strand 200 may form a conductor 300 for use in an implantable medical device. Alternatively, a conductor 300 may comprise a plurality of strands 200 that may be parallel (e.g., FIG. 6), twisted around one another (e.g., FIG. 7), braided, or the like. A conductor 300 may contain any suitable number of strands 200. In some embodiments, a conductor includes one strand, three strands, seven strands, or nineteen strands.

In some embodiments, a conductor is oriented in a 1×7, 7×7, 1×19, or 1×3 configuration, where the first number indicates the number of wires in a strand and the second number indicates the number of strands in conductor. Of course, a conductor may have any other suitable configuration. For purposes of the present disclosure, where there is one wire in a strand (e.g., 1×7, 1×19, 1×3) the combination of wires can be considered the strand and the strand can thus be considered the conductor. For example, if a 1×7 configuration is employed, the conductor can be considered to be of a single strand having seven wires.

Figure 8:
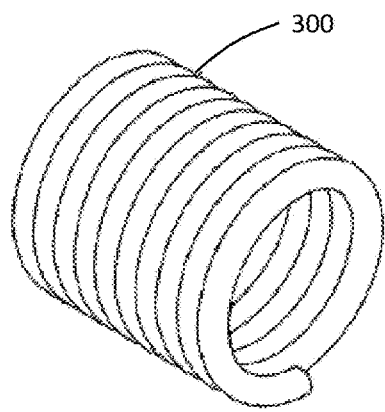
FIG. 8 is a schematic perspective view of a portion of an embodiment of a conductor.

Often, a conductor in an implantable medical lead is coiled (see, e.g., conductor 300 in FIG. 8). The conductor 300 may be coiled prior to, or as a part of, assembling a lead. In some embodiments, the conductor 300 is coiled about a mandrel prior to incorporation into the lead.

Whether a conductor, strand, or filar is coiled, twisted or braided, it can be beneficial to heat the structure to relieve stress.

A filar, strand, or cable as described herein may be electrically insulated by an insulating layer (not shown), which may be a polymer. Examples of insulating polymers that can be used include ethylene tetrafluoroethylene (ETFE), polytetrafluoroethylene (PTFE), silicone rubber, polyimide and polyurethane. Other materials that act as electrical insulators may be used. In some embodiments, the filar, strand or cable is anodized to form an outer oxide layer that can serve as an insulator. In many embodiments, the insulating layer extends the length of the filar, strand or cable, which may be a coil. A portion of the insulating layer may be removed for purposes of forming an electrical contact with, for example, and electrode or to form an electrode.

In some embodiments, insulating layers or liners that can be used in conjunction with the present disclosure are shown and described with respect to U.S. Pat. No. 8,005,549 issued Aug. 23, 2011, U.S. Pat. No. 7,783,365 issued Aug. 24, 2010, and assigned to the assignee of the present invention, the disclosure of which are hereby incorporated herein by reference in their entirety to the extent that they do not conflict with the disclosure presented herein.

Figure 9:
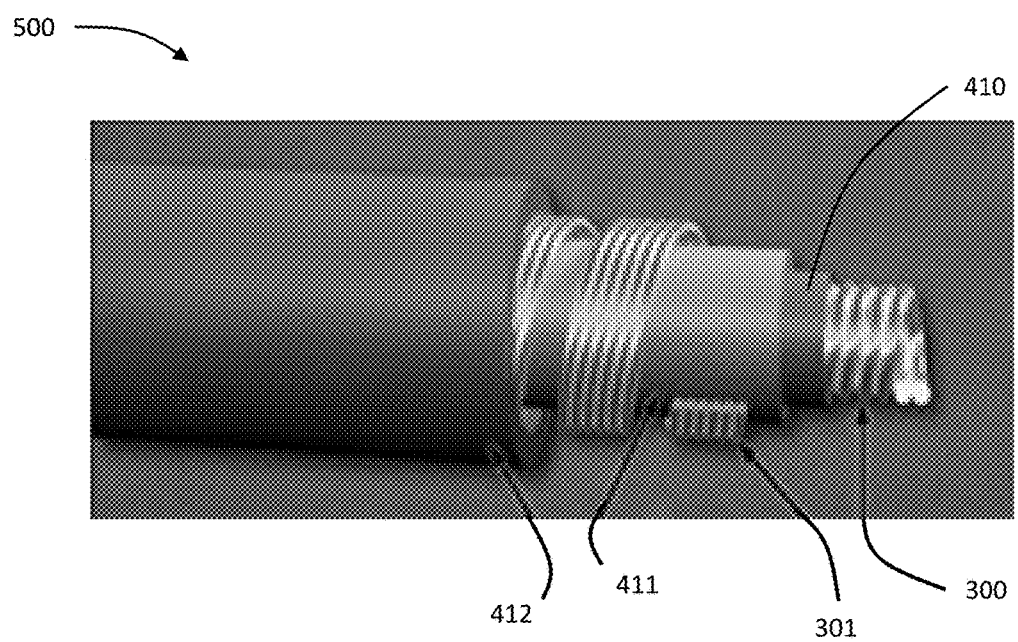
FIG. 9 is a schematic partial cut away perspective view of an embodiment of a lead.

Referring now to FIG. 9, a partial cut-away perspective view of an embodiment of a lead 500 is shown. The lead includes two coiled conductors 300, 301. A layer of insulating material 410 is disposed over conductor 300, while conductor 301 is spirally wound over insulating material 411. A layer of insulating material 412 is disposed over conductor 301 and serves as the outer layer of the lead 500. The lead depicted in FIG. 9 is shown for purposes of example.

It will be understood that a lead may have any suitable number of conductors and any suitable configuration. Insulating layers may be coated, or otherwise disposed, on an underlying layer or structure. Insulating layer is electrically insulating and is preferably biocompatible. Where a lead includes more than one insulating layer, it will be understood that the materials, thicknesses, etc. of the insulating layers may be the same or different. Examples of materials that are suitable for insulating layers of leads include silicon, polyurethane, polytetrafluoroethylene, poly(ethylene-co-tetrafluoroethylene), polyimide, copolymers of silicon and polyurethane, and the like. Insulating layers may have any suitable thickness. For example, insulating layers can have a thickness of from about 0.0001 inch to about 0.01 inch, such as from about 0.0003 inch to about 0.002 inch.

Any suitable implantable medical lead may include a conductor as described herein. For example, a lead may be a lead for providing therapy to a patient, a lead for monitoring a condition of a patient, or a lead for therapy and monitoring. Examples of such leads include leads for cardiac monitoring or therapy, brain and spinal cord monitoring or therapy, gastrointestinal monitoring or therapy, peripheral nerve monitoring or therapy, muscular monitoring or therapy, and the like. For example, a lead may be a pacemaker lead, a defibrillator lead, a cardiac resynchronization lead, a cardiac monitoring lead, a deep brain stimulation lead, a spinal cord stimulation lead, a peripheral nerve stimulation lead, or the like.

Such leads typically have a distal end portion having one or more electrodes for delivering therapy or monitoring a condition of a patient. The leads also have a proximal end portion having one or more electrical contacts configured to electrically couple with an active medical device, such as a signal generating device, a monitoring device, or the like. Examples of such active medical devices include a pacemaker, a defibrillator, a cardiac resynchronization device, a cardiac monitoring device, a deep brain stimulator, a spinal cord stimulator, a peripheral nerve stimulator, a gastro stimulator, and the like. The proximal contacts of the leads are electrically coupled to the electrodes via one or more conductors (e.g., filars, strands, cables or coils) as described herein.

Figure 10:
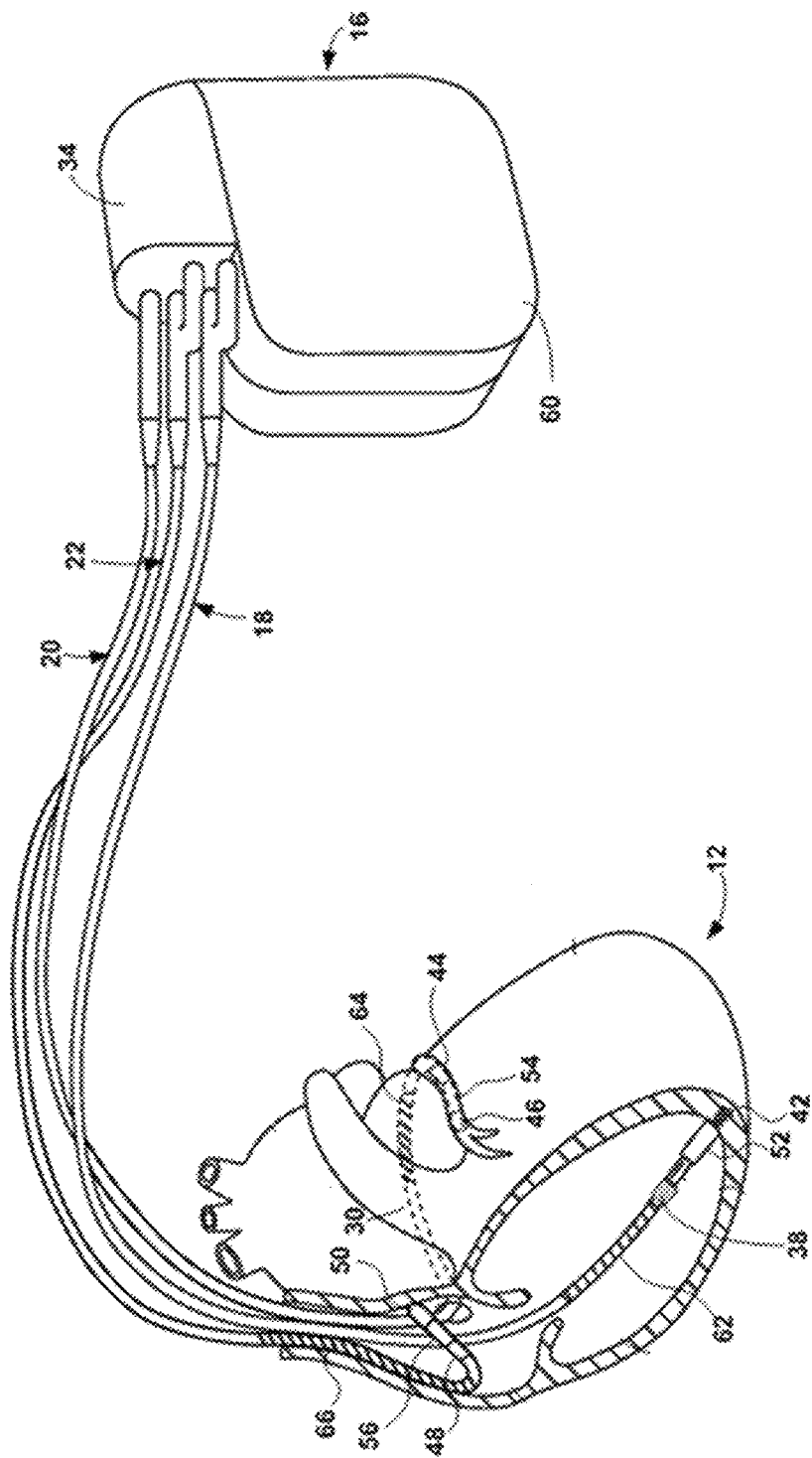
FIG. 10 is a conceptual view of an embodiment of an active medical device and embodiments of associated leads for monitoring or delivering therapy to a heart.

For purposes of further example, a conceptual schematic diagram of an embodiment of a system including an implantable active medical device, IMD, 16 and leads 18, 20, 22 is shown in FIG. 10. Leads 18, 20, 22 may be electrically coupled to a stimulation generator, a sensing module, or other modules of IMD 16 via connector block 34. In some examples, proximal ends of leads 18, 20, 22 may include electrical contacts that electrically couple to respective electrical contacts within connector block 34. In addition, in some examples, leads 18, 20, 22 may be mechanically coupled to connector block 34 with the aid of set screws, connection pins or another suitable mechanical coupling mechanism.

In some embodiments, connector block 34 includes connector modules as described in U.S. Pat. No. 7,601,033 issued Oct. 13, 2009, U.S. Pat. No. 7,654,843 issued Feb. 2, 2010, and assigned to the assignee of the present invention, the disclosure of which are hereby incorporated herein by reference in their respective entireties to the extent that they do not conflict with the disclosure presented herein.

Each of the leads 18, 20, 22 includes an elongated insulative lead body, which may carry a number of concentric coiled conductors separated from one another by tubular insulative sheaths. In the illustrated example, an optional pressure sensor 38, such as a capacitive or piezoelectric absolute pressure sensor, and bipolar electrodes 40 and 42 are located proximate to a distal end of lead 18. In addition, bipolar electrodes 44 and 46 are located proximate to a distal end of lead 20 and bipolar electrodes 48 and 50 are located proximate to a distal end of lead 22.

Electrodes 40, 44 and 48 may take the form of ring electrodes, and electrodes 42, 46 and 50 may take the form of extendable helix tip electrodes mounted retractably within insulative electrode heads 52, 54 and 56, respectively. It will be understood that any suitable electrode may be employed in accordance with the teachings presented herein and that the electrodes need not be limited to ring electrodes or helix tip electrodes. Each of the electrodes 40, 42, 44, 46, 48 and 50 may be electrically coupled to a respective one of the coiled conductors within the lead body of its associated lead 18, 20, 22, and thereby coupled to respective ones of the electrical contacts on the proximal end of leads 18, 20 and 22. In some embodiments, a portion of the conductor can be exposed outside of the lead body and can serve as an electrode.

Electrodes 40, 42, 44, 46, 48 and 50 may sense electrical signals attendant to the depolarization and repolarization of heart 12. The electrical signals are conducted to IMD 16 via the respective leads 18, 20, 22. IMD 16 may also deliver pacing pulses via electrodes 40, 42, 44, 46, 48 and 50 to cause depolarization of cardiac tissue of heart 12. In some examples, IMD 16 includes one or more housing electrodes which may be formed integrally with an outer surface of hermetically-sealed housing 60 of IMD 16 or otherwise coupled to housing 60. In some examples, housing electrode is defined by an uninsulated portion of an outward facing portion of housing 60 of IMD 16. Other division between insulated and uninsulated portions of housing 60 may be employed to define two or more housing electrodes. In some examples, housing electrode comprises substantially all of housing 60. Any of the electrodes 40, 42, 44, 46, 48 and 50 may be used for unipolar sensing or pacing in combination with housing electrode 58.

In some embodiments, at least two of the electrodes, 42, 44, 46, 48, 50 take the form of ring and barrel shaped electrodes, respectively, provided with ring-shaped steroid eluting Monolithic Controlled Release Device (MCRD) as described in U.S. Pat. No. 8,825,180 by Bauer, et al., hereby incorporated herein by reference in its entirety to the extent that it does not conflict with the disclosure presented herein. Other known electrode designs may of course be substituted Leads 18, 20, 22 may also include elongated electrodes 62, 64, 66, respectively, which may take the form of a coil. IMD 16 may deliver defibrillation shocks to heart 12 via any combination of elongated electrodes 62, 64, 66, and housing electrode. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy, tantalum, tantalum alloys, MP35N, coated metals or other materials known to be usable in implantable defibrillation electrodes.

In some embodiments, one or more lead 18, 20, 22 is an active fixation leads as described in U.S. Pat. No. 7,860,580, issued to Falk, et al., U.S. Pat. No. 7,532,939, issued to Sommer, et al. and U.S. patent application Ser. No. 13/793, 622, filed Mar. 11, 2013 by Sommer, et al., all of which are hereby incorporated herein by reference in their respective entireties to the extent that they do not conflict with the present disclosure.

It will be understood that leads as described herein may be used with any suitable system, such as a deep brain stimulation system, a spinal cord stimulation system, a gastric stimulation system, a monitoring system, and the like, and that the cardiac stimulation and monitoring system presented in FIG. 10 is merely for purposes of example.

Figure 11:
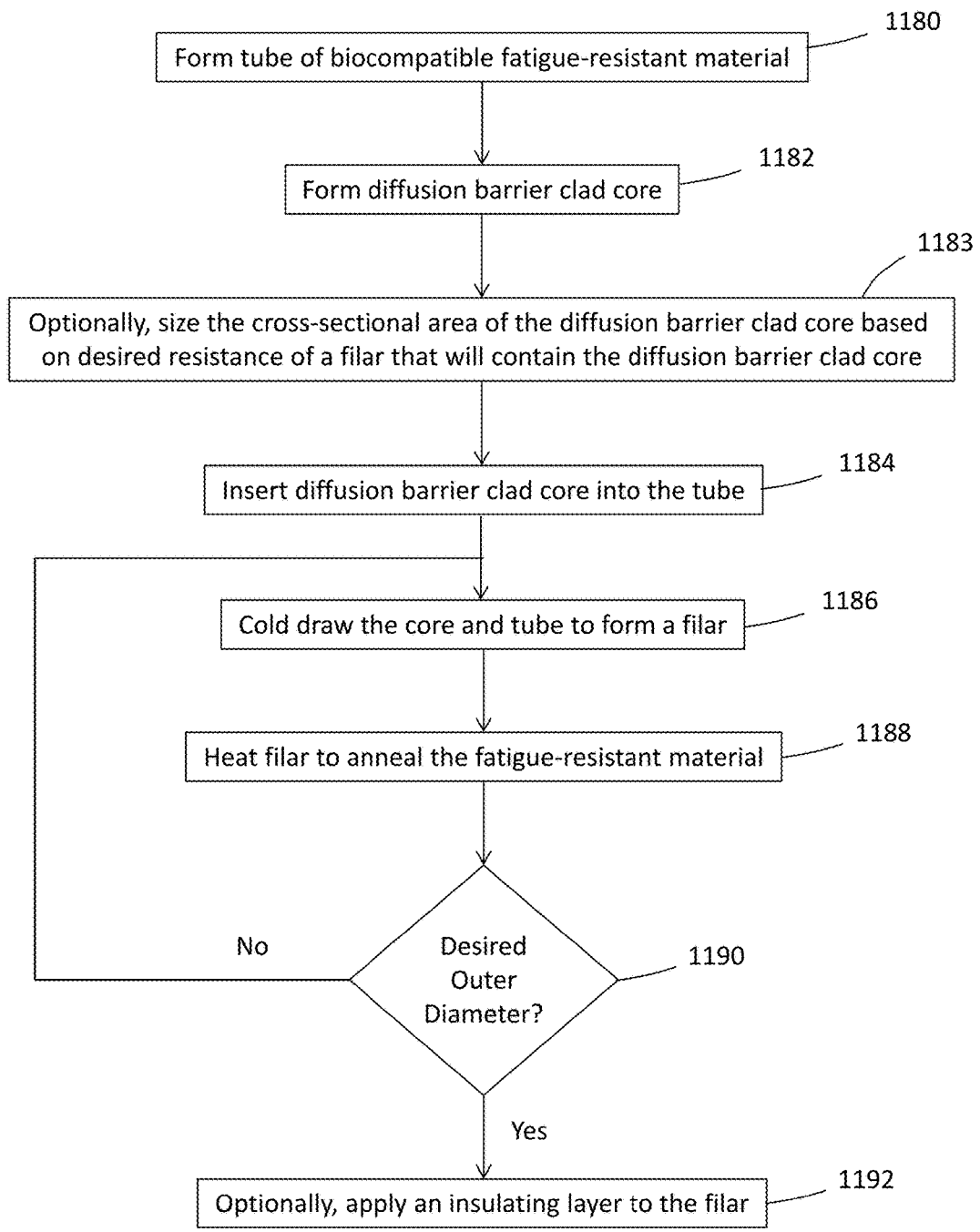
FIG. 11 is a flow diagram of one method of forming a wire according to one example of the disclosure.
Figure 12:
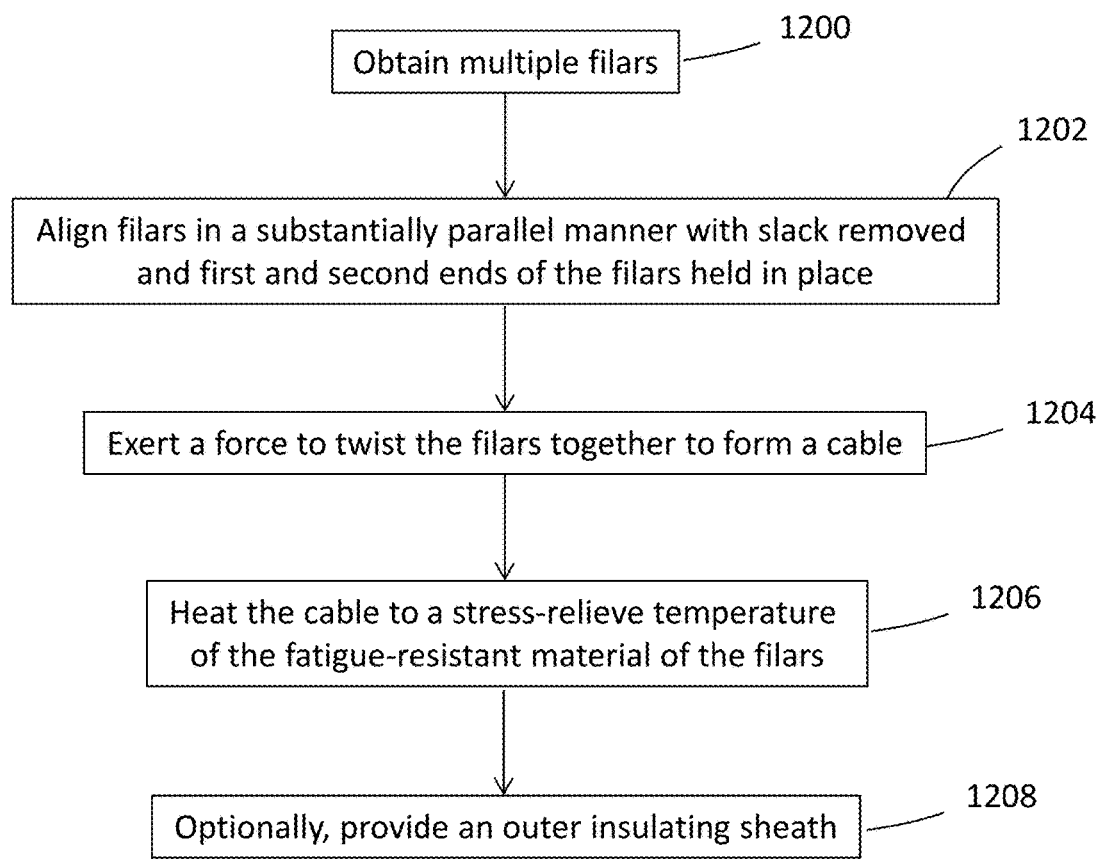
FIG. 12 is a flow diagram of a process according to one specific cable embodiment of the current disclosure.
Figure 13:
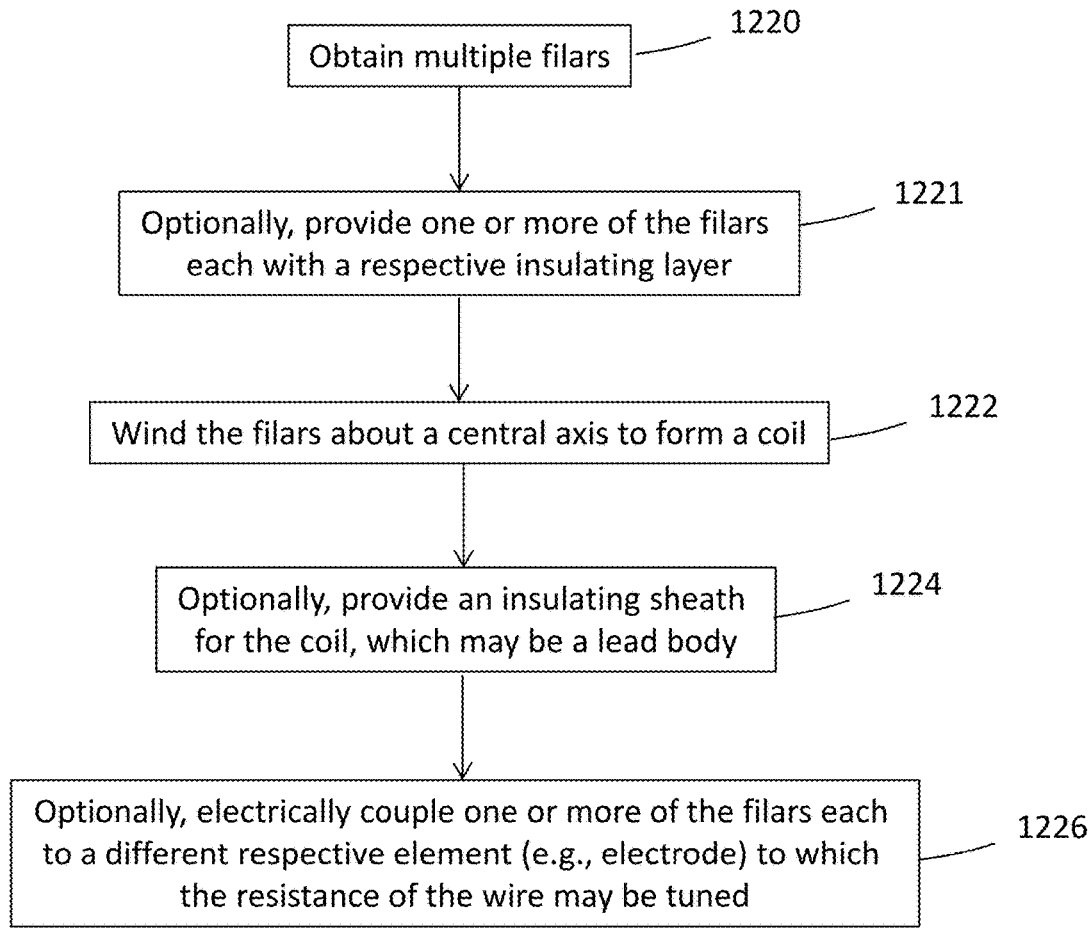
FIG. 13 is a flow diagram of another process according to one specific coil embodiment of the current disclosure.

For purposes of example, flow diagrams of embodiments of methods for forming filars or cables are shown in FIGS. 11-13.

FIG. 11 is a flow diagram of one method of forming a filar according to one example of the disclosure. First, a tube is formed of a fatigue-resistant metallic material, such as biocompatible titanium alloy (1180). The tube may have an inner diameter of from about 0.1 inches to about 2 inches (or from about 0.25 cm=to about 5.0 cm). Next, a diffusion barrier clad core may be formed of material possessing a resistivity of less than 25 micro-ohm-cm (the core) and properties to prevent intermetallic diffusion of the core with the fatigue-resistant layer formed from the tube (the diffusion barrier) (1182). Silver, which has a resistivity of 1 micro-ohm-cm may be used as the core, and MP35N alloy may be used as the diffusion barrier. The core and diffusion barrier may be formed by cold-working the core material, or by heating and drawing the material. The diameter of the final core and diffusion barrier is use-dependent and is sized to readily be inserted within the inner lumen of the fatigue-resistant tube.

In one example, the diameter of the diffusion barrier clad core may optionally be sized so that after a filar has been drawn from the tube and diffusion barrier clad core, the filar will have a desired predetermined resistance (1183). In particular, the core diameter may be selected so that, in the finished filar, the core cross-sectional area is a predetermined percentage of the cross-sectional area of the filar. In this manner, the resistance of the end-product filar is selectable, and may be tuned for a particular application. For instance, the core may be formed to have a relatively large cross-sectional area if a relativity low resistance wire is desired. Alternatively, a relatively small cross-sectional area may be selected for the core if the resulting wire is to have a higher resistance. The selected resistance of the filar may be tuned to that of an interconnecting structure such as a conducting or connector electrode.

The diffusion barrier clad core may be inserted into the tube (1184), and the diffusion barrier clad core and tube may be cold drawn (as in drawing it through a die of a predetermined size) to form a filar. (1186). This filar may be heated to annealed the fatigue-resistant material (1188). This annealing step will change the physical properties of the filar, allowing the filar to retain ductility so that it may optionally be submitted to another cold drawing step.

If a filar having a desired outer diameter has been obtained (1190), processing may continue to step 1192 where a layer of insulating material may optionally be applied to the filar. In one example, this involves dipping the filar in a liquefied ETFE to coat the filar, and then allowing the insulation material to solidify. Any other biocompatible insulating material may be used instead as discussed herein, and other processes such as extrusion may be used to apply this material.

If the desired outer diameter has not been obtained in step 1190, processing may return to step 1186 wherein the filar is re-drawn through another die having yet a smaller diameter and the filar is re-heated as shown in step 1188. Steps 1186 and 1188 may be repeated any number of times to obtain a filar having a desired diameter.

FIG. 11 depicts a process where the production route includes first obtaining a diffusion cladded core (step 1183). However, it will be understood that the process can be readily changed to forming a fatigue-resistant cladded barrier prior to insertion of a conductive core. Such changes are contemplated herein.

FIG. 12 is an example flow diagram of a manufacturing process according to one specific cable embodiment of the current disclosure. Multiple filars as described herein may be obtained (1200). It will be understood that all of the filars used to form a cable need not be the same and each filar need not include a conductive core, diffusion barrier, and fatigue-resistant metallic layer as described herein. One or more of the filars employed to form a cable may optionally have an electrically insulating coating.

Next, the filars may be aligned in a substantially parallel manner with slack removed and ends of the filars being held securely in place (1202). A force may be exerted at first ends of the filars, or opposing forces may be exerted on both ends of the filars to twist the filars together to form a cable (1204). This may be accomplished by threading ends of filars into retaining members and twisting one or more of the retaining members as filars are uncoiled from spools, thereby forming the twisted cable. The cable may then be heated to a stress-relieve temperature of the fatigue-resistant material (1206). A particular embodiment heats the cable to a range from about 500° C. to about 650° C. for less than 20 seconds for filars containing Ti-15Mo as the fatigue-resistant metallic layer. One specific scenario uses a temperature of 625° C., which is maintained for less than 10 seconds. This heating will change the physical properties of the cable, allowing the cable to remain twisted even after the twisting force is removed.

An outer insulating sheath may optionally be provided (1208). For instance, the cable may be dipped in liquefied ETFE. Any other biocompatible insulating material may be used for this purpose. Alternatively, an extrusion process may be used to apply the insulating sheath to the cable.

FIG. 13 is a flow diagram of another manufacturing process according to one specific coil embodiment of the current disclosure. Multiple filars as described herein are obtained (1220). For instance, twelve such filars may be obtained. Optionally, one or more of these filars may be provided with a respective insulating layer (1221). The filars may be wound about a central axis to form a multi-filar coil (1222).

In one instance, the filars are wound around a mandrel to form the coil, with the mandrel being removed after winding is completed. In a specific example, at least some of the multiple filars may be electrically insulated one from another or all of the filars may be insulated in this manner. This may be achieved by providing each of the wires used to form the coil with a respective insulating coating, such as a coating of ETFE.

Optionally, an insulating sheath may be provided for the coil (1224). In one embodiment, the insulating sheath may be a lead body that carries the coil. One or more of the filars of the coil may each be electrically and mechanically coupled to a different respective element, such as a conducting electrode or a connector electrode or contact (1226). In a specific embodiment, each of the filars may be coupled to a different conducting/connector electrode pair to transmit a respective electrical signal therebetween. Thus, in the specific scenario wherein the coil includes twelve filars, up to twelve conducting/connector electrode pairs may be so connected to independently transmit twelve signals simultaneously via the filars of the coil. In some examples, one or more filars carrying cores may optionally have resistances that are tuned to approximate or match the resistances of element(s) to which the filar(s) are coupled. In some embodiments, a portion of the fatigue-resistant metallic layer may be removed to form a joint between the electrode and the filar if the diffusion barrier and the electrode can form a more suitable joint than the fatigue-resistant material and the electrode.

In another example, the inner lumen of the coil defines a space that may receive a guiding device such as a stylet, guide wire, or some other guiding mechanism that can be used to position the coil (and the device that carries the coil) within a living body.

DEFINITIONS

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like. As used herein, "consisting essentially of," as it relates to a product, method or the like, means that the components of the, product, method or the like are limited to the enumerated components and any other components that do not materially affect the basic and novel characteristic(s) of the composition, product, method or the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Also herein, the recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" a particular value, that value is included within the range.

As used herein, the term "about" encompasses the range of experimental error that occurs in any measurement or ranges within manufacturing tolerances.

As used herein, a "brittle" material or layer, such as an intermetallic layer, is a material or layer that breaks without significant deformation (strain) when subjected to stress.

As used herein, "prevents," in the context of a diffusion barrier preventing intermetallic diffusion between the core and the fatigue-resistant layer, means that the diffusion barrier inhibits diffusion or retards the rate of diffusion to an extent that fatigue performance is not appreciably affected by formation of a brittle intermetallic layer due to diffusion between the core and the fatigue-resistant layer or alloying of the fatigue-resistant layer such that ductility or fatigue performance of that material suffers. It will be understood that some species from the core or the fatigue-resistance layer can diffuse through the diffusion barrier, but the diffusion barrier prevents or retards most of such diffusion.

As used herein, a "drawing process," as it relates to drawing composite filars, is a process that includes drawing a filar through a die and subsequent heating or annealing that may be performed to relieve stress in the filar due to drawing through the die.

As used herein, "radiopaque: materials are those that inhibit passage of electromagnetic radiation, particularly X-rays. Using analog X-ray films, such materials have a whiter appearance compared with a relatively dark appearance of more radiolucent materials. Digital X-ray images usually appear inverted such that radiopaque components appear dark gray or black. To determine whether a particular medical device component, e.g., a diffusion barrier, may be sufficiently radiopaque for the intended implant location in a human patient, a designer may utilize ASTM G640-12 "Standard Test Methods for Determining Radiopacity for Medical Use."

INCORPORATION BY REFERENCE

Any patent or non-patent literature cited herein is hereby incorporated herein by reference in its entirety to the extent that it does not conflict with the disclosure presented herein.

In the detailed description above several specific embodiments of systems, leads, conductors, strands, wires and methods are disclosed. It is to be understood that other embodiments are contemplated and may be made without departing from the scope or spirit of the present disclosure. The detailed description, therefore, is not to be taken in a limiting sense.

Thus, systems, devices and methods for COMPOSITE FILAR FOR IMPLANTABLE MEDICAL DEVICE are described. Those skilled in the art will recognize that the preferred embodiments described herein may be altered or amended without departing from the true spirit and scope of the disclosure, as defined in the accompanying claims.

The invention claimed is:

1. A composite filar for use in an implantable medical device, the filar comprising:
a metallic core having a resistivity of less than 25 micro-ohm-cm;
a metallic diffusion barrier disposed about and in contact with the core; and
a fatigue-resistant metallic layer disposed about and in contact with the diffusion barrier,
wherein the diffusion barrier prevents intermetallic diffusion between the core and the fatigue-resistant layer, and
wherein the fatigue-resistant metallic layer has an elastic modulus ranging from 30 GPa to 90 GPa.

2. A composite filar according to claim 1, wherein fatigue performance of the filar is at least three times greater than a similar filar that does not include the fatigue-resistant metallic layer disposed about the diffusion barrier when fatigue performance is determined by ASTM E2948-14, Standard Test Method for Conducting Rotating Bending Fatigue Tests of Solid Round Fine Wire.

3. A composite filar according to claim 1, wherein the fatigue performance of the filar is at least five times greater than a similar filar that does not include the fatigue-resistant metallic layer disposed about the diffusion barrier when fatigue performance is determined by ASTM E2948-14, Standard Test Method for Conducting Rotating Bending Fatigue Tests of Solid Round Fine Wire.

4. A composite filar according to claim 1, wherein the fatigue-resistant metallic layer comprises a titanium alloy comprising one or more of molybdenum, niobium, tantalum, zirconium, chromium, iron and tin.

5. A composite filar according to claim 1, wherein the metallic layer comprises a titanium-molybdenum alloy.

6. A composite filar according to claim 1, wherein the metallic core comprises one or more metal selected from the group consisting of: silver; tantalum, a tantalum alloy comprising one or more of Mo, Nb, Zr, W and Pd; niobium, a niobium alloy comprising one or more of Ta, Mo, Zr, W, Pt, and Pt); platinum; a platinum alloy; palladium; a palladium alloy comprising one or both of Re and Rh; and gold.

7. A composite filar according to claim 1, wherein the metallic core comprises silver.

8. A composite filar according to claim 1, wherein metallic core consists essentially of silver.

9. A composite filar according to claim 1, wherein the diffusion barrier comprises a radiopaque material.

10. A composite filar according to claim 1, wherein the diffusion barrier comprises a nickel-cobalt-molybdenum-chromium alloy.

11. A composite filar according to claim 1, wherein the diffusion barrier comprises an alloy comprising 33% to 37% by weight nickel, 31.5% to 39% by weight cobalt, 9% to 10.5% by weight molybdenum, and 19% to 21% by weight chromium.

12. A composite filar according to claim 1, wherein the core, the diffusion barrier, and the metallic layer are capable of being cold-drawn.

13. A composite filar according to claim 1, further comprising an insulating layer disposed about the metallic layer.

14. A conductive cable comprising two or more filars according to claim 1.

15. A conductive cable according to claim 14, wherein at least two of the two or more filars are twisted about each other.

16. An implantable medical lead comprising a filar according to claim 1.

17. An implantable medical lead according to claim 16, wherein the filar is coiled about a longitudinal axis of the lead.

18. A composite filar for use in an implantable medical device, the filar comprising:
a core comprising silver;
a diffusion barrier disposed about and in contact with the core, the diffusion barrier comprising an alloy comprising 33% to 37% by weight nickel, 31.5% to 39% by weight cobalt, 9% to 10.5% by weight molybdenum, and 19% to 21% by weight chromium; and a metallic layer comprising a titanium-molybdenum alloy disposed about and in contact with the diffusion barrier.

* * * * *